United States Patent [19]

Daneshvar

[11] Patent Number: 5,507,284
[45] Date of Patent: Apr. 16, 1996

[54] AIRWAY SECURING SYSTEM

[76] Inventor: Yousef Daneshvar, 21459 Woodfarm, Northville, Mich. 48167

[21] Appl. No.: 127,180

[22] Filed: Sep. 27, 1993

[51] Int. Cl.⁶ .................................................. A61M 16/00
[52] U.S. Cl. ............................... 128/207.14; 128/207.15; 128/200.26
[58] Field of Search ......................... 128/200.26, 207.14, 128/207.15

[56]  References Cited

U.S. PATENT DOCUMENTS

| 3,659,611 | 5/1972 | Miller | 128/207.15 |
| 4,156,428 | 5/1979 | Henkin | 128/207.15 |
| 4,850,371 | 7/1989 | Broadhurst et al. | 128/207.14 |
| 4,928,687 | 5/1990 | Lampotang et al. | 128/200.26 |
| 5,040,531 | 8/1991 | Coleman et al. | 128/207.14 |
| 5,060,647 | 10/1991 | Alessi | 128/207.14 |

*Primary Examiner*—Edgar S. Burr
*Assistant Examiner*—Aaron J. Lewis

[57]  ABSTRACT

An airway securing system introduces a new means of securing the airway system in patients during a cardiopulmonary resuscitation. The system shows a modified and improved version of an endotracheal tube as well as an esophageal tube that can be also held in place securely by a support unit. The system includes new pieces which may be used to open a patient's mouth which are believed to save more human lives in critical moments.

14 Claims, 7 Drawing Sheets

AIRWAY SECURING SYSTEM

THE BACKGROUND OF THIS INVENTION

Saving a person faced with the condition of sudden death is a great achievement and this inventor wishes to be part of such an important job. This is by introducing his ideas which relates to making a new means of intubation and securing the air way of patients during the Cardiopulmonary resuscitation. The units he introduces are combinations of units that although may be used separately but in order to reach a favorable result they need to be used one after another in order to secure the airway of these critically ill patients. This invention introduces a new intubation tubes that are believed to be far better and less traumatic than the old ones. New ways of opening mouth of a patient who is unconscious, and closing the esophagus of a patient that is being resuscitated for prevention of expulsion of stomach contents into the oropharynx are parts of this invention. A proper box that will provide lights and suction machine and cassette recorder is also believed to be helpful in many cases. For making this invention, the inventor is using his experience during his practice of medicine for over twenty three years. He has observed that intubation of patients during resuscitation have not been easy for every one. And the desperately needed air and the oxygen does not reach quickly to many of these patients whose life depends on them. The solution has not been easily and the experienced physicians and medical staff are not there all the time around the clock every where, when a patient suddenly needs to be resuscitated. It should also be alarmingly noted that the introduction of the AIDs virus has made the general public and even the medical staff very reluctant to provide mouth to mouth resuscitation and in these circumstances providing an effective airway even gets more important and serious issue than before. However the present equipments need a lot of experience for being used properly. This back ground plus having some of his own patients who has complained for many days after being intubated had made the inventor to believe that the endotracheal tubes were faulty and someway were causing pain in throat. Furthermore he also has noticed how devastating and problematic it is to have the contents of the stomach of some patients to come up into their mouth and the whole pharynx and larynx. Which makes a very messy condition and would cause many sever complications. For these reasons he has thought about making units that an esophageal tube with a balloon or balloons around it to be used to prevent from the food coming out of the esophagus. These devices are best to be used all together to complement each other so that they collectively diminish those problems and to give a better and less complicated chance of survival for patients who are about to loose their only life once and for all.

THE BRIEF EXPLANATION OF THE INVENTION

This application introduces a new units for initiation and maintaining the airways in a patient who needs intubation and Cardiopulmonary resuscitation. This invention first introduces a unit that will function like a jack in order to open the mouth of such patients when their teeth clinches and prevents the medical staff to secure their airway. Second it shows how a new airway may be used to keep the tongue down and to have a balloon as well in order to open and secure a space in the mouth to be used for intubation of these patients. Third a special endotracheal tube is introduced with a shape in its laryngeal area that would not cause as much stress and injury to the vocal cords. A mini light is also incorporated in front surface of these endotracheal tubes to help to locate the position of their tip in a patient. Some of these endotracheal tubes may be made to have webs instead of balloons to prevent from air leak. A new esophageal tube is also introduced that has bulbs or webs in its outer surface to prevent from the stomach contents of patients to come up during resuscitation and therapy to cause a serious complications. A new laryngoscopes area also introduced as well with beliefs that will help to intubate a patient easier. A special box that will provide lights and suction machine and cassette recorder is also introduced and is believed to be helpful in many cases. There will be a system to incorporate all of these units together so that a complete unit could be presented when needed to have every needed means and materials for securing the airway of a patient. The inventor has the hope that these units collectively with the related teachings to improve the present conditions of Cardiopulmonary resuscitation for a better results.

THE DETAILED EXPLANATION OF THE FIGURES

Figure 1:
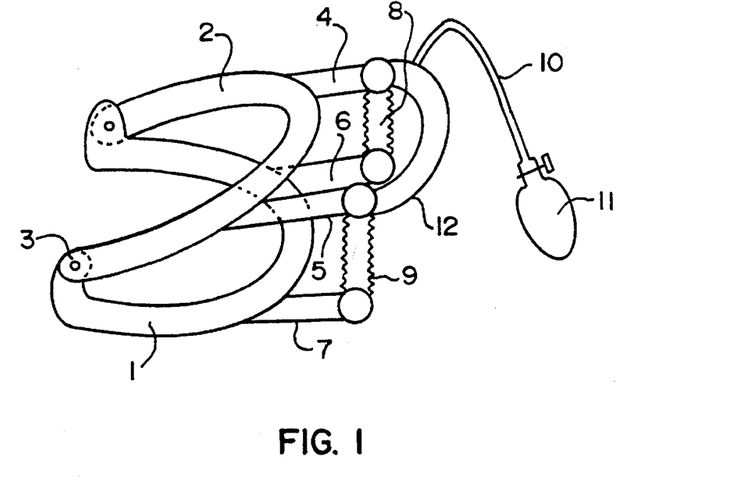
FIG. 1. This fig shows a mouth opener which is made from hinging two pieces of 1 and 2 at 3. This unit has a system in front to allow to open these two pieces by jacking system and to open the mouth.

FIG. 1. This fig shows a mouth opener which is made from hinging two pieces of 1 and 2 at 3. The tip of the lower part 1 is extended in rear above its upper surface and this is intentional. The sides 1 and 2 both have an extension in their front/side which in the upper piece of 2 they are marked at 4 and 6. And in the lower piece of 1 at 5 and 7. These pieces are connected to their upper counterpart by a mean of elevation here shown by 8 and 9. So that inflation of the upper ends of these special pieces of 8 and 9 will separate the no 1 and 2 and to open the mouth. At the time of use this piece will be placed inside the mouth outside of the teeth and gum and inside the cheek. So that with inflation the front part of this will be separated to open mouth.

Figure 2:
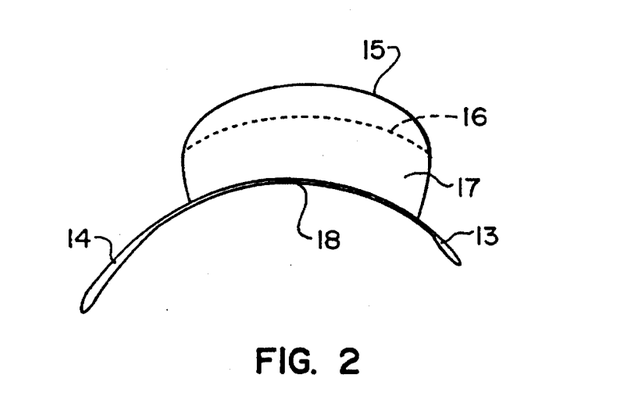
FIG. 2. This is schematical side view of a special tongue presser that has a lower hard plastic plate.

FIG. 2. This is schematical view to show the side view of a special tongue presser that has a lower hard plastic plate of 18 which is curved to match the shape of the tongue. The front tip of this unit is shown in 13 and its handle at 14. The 15 shows the upper surface of a balloon which is over the hard plastic plate of 16 which is placed inside this balloon. No 17 points to a space which will be open under the plastic plate 16 and above plastic 18. At the time of use the plastic piece 18 will be placed into the mouth and over the tongue then with inflation of the balloon 19 shown in FIG. 3 this unit will be functional and will move the piece 16 higher to create the space 17. A thin band of plastic may hold these balloons and related parts in place flat to be entered into the mouth then to be ripped off after the balloon is inflated.

Figure 3:
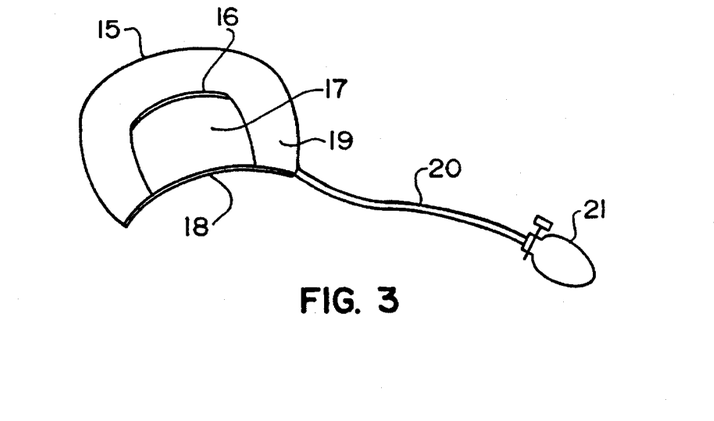
FIG. 3. This is another schematical view of a unit similar to one shown in FIG. 2 with a balloon, when the balloon is inflated.

FIG. 3. This is another schematical view which shows the front view of a special tongue presser similar to one shown in previous picture of 2 when it is inflated. In this fig the lower plate 18 is shown with balloon 19 on it. The upper surface of this balloon 15 is shown. The empty space 17 is marked. The plate 16 and the inflation tube of 20 and inflation bulb 21 are also shown.

Figure 4:
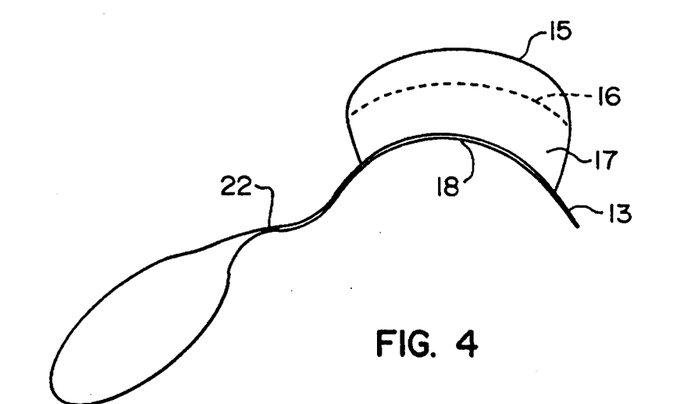
FIG. 4. This fig shows a tongue pressure similar to one shown in FIG. 2. Which has a larger handle of 22 for a better control.

FIG. 4. This fig shows a tongue pressure similar to one shown in FIG. 2. Which has a larger handle of 22 for a better control. In this fig again the bottom hard plate of 18 is shown and front tip of this unit is shown in 13. The 15 shows the upper surface of a balloon which is over the hard plastic plate of 16 which is placed inside this balloon. No 17 points to an open space under the plastic plate 16 and above plastic 18. At the time of use the plastic piece 18 will be placed into the mouth and over the tongue then with inflation of the balloon 19 shown in FIG. 3 this unit will be functional and will move the piece 16 higher to create the space 17.

Figure 5:
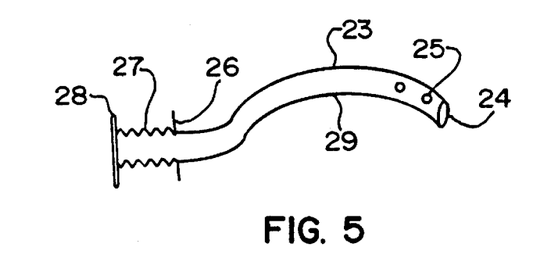
FIG. 5. This fig shows the side view of an air way that will be a curved tube in the shape shown.

FIG. 5. This fig shows the side view of an air way that will be a curved tube in the shape shown. Which will have opening inside along its length to open at 24. And with holes of 25 and one next to it in its side. The wall 26 is to stand outside of the lips and the space between walls 28 and 26 has the indentations of 27 that will allow a unit to be stuck to it to hold it conveniently in place.

Figure 6:
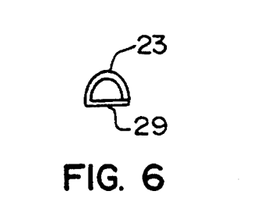
FIG. 6. This fig shows the cross cut view of an air way similar to one shown in previous fig of 5.

FIG. 6. This fig shows the cross cut view of an air way similar to one shown in previous fig of 5. in point between 23 and 24 from previous fig in shown the flat bottom of 29 with top surface of 23 and the opening in its center.

Figure 7:
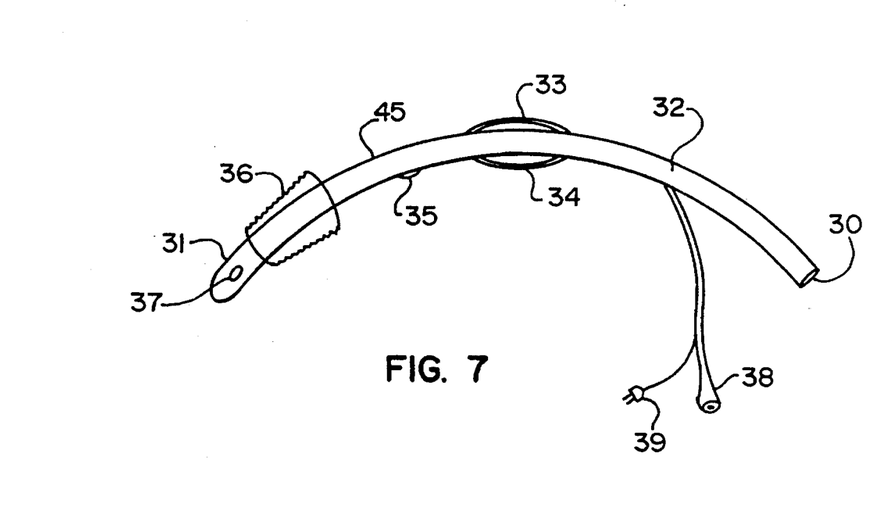
FIG. 7. This fig shows the side view of an endotracheal tube which has a special shape in a segment of its wall that will stand in the laryngeal area.

FIG. 7. This fig shows the side view of an endotracheal tube which has a special shape in a segment of its wall that will stand in the laryngeal area. Also it has a light 35 that will cause the illumination to occur and to allow its position to be seen. In this fig the curved tip of this unit is shown at 31 with a hole 37 in it. The outer tip at 30 which will be connected to the air bag or respirator by an adaptor (shown in FIG. 11). The body of this unit is marked at 32 and the front curve of the laryngeal part by 34 and the rear curve of it by 33. The bulb by 35 and the balloon by 36. The inflation port by 38 and the connection part to battery by 39.

Figure 8:
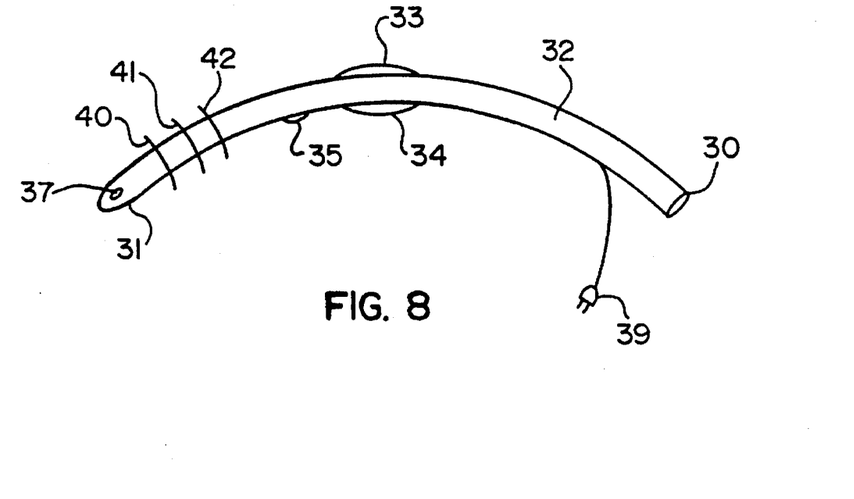
FIG. 8. This fig shows an endotracheal tube which instead of the balloon 36 of previous fig has a series of soft plastic walls 40, 41, 42

FIG. 8. This fig shows the side view of an endotracheal tube which is very similar to the unit shown in previous fig of 7. Except this unit instead of the balloon 36 has a series of soft plastic walls 40, 41, 42 which will stand like a wall between the inner wall of the trachea and outer wall of the endotracheal tube to prevent from air leak around this tube. In this fig the curved tip of this unit is shown at 31 with a hole 37 in its side. The outer tip at 30 which will be connected to the air bag or respirator by an adaptor (shown in FIG. 11). The body of this unit is marked at 32 and the front curve of the laryngeal part by 34 and the rear curve of it by 33. The bulb by 35 and the connection part to the battery by 39.

Figure 9:
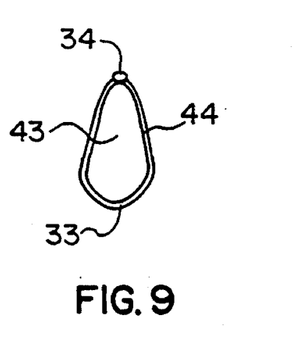
FIG. 9. This is a cross cut view of the endotracheal tube shown in previous fig of 7 in the area between the line 33–34. Which has a rather modified triangular shape as shown.

FIG. 9. This is a cross cut view of the endotracheal tube shown in previous fig of 7 in the area between the line 33–34. This shows how the cross cut of this tube in this spot, and how it is not round or circular shaped but rather a somewhat modified triangular shape or so as shown. This shape is chosen in order to match the shape of the larynx of the human being in the vocal cord area (in resting and functional state). In this view the open center is shown by 43 and the front line by tip 34 (That can carry the inflation tube as well as the wire of the bulb). The rear line is shown by point 33. The side wall of 44 is also marked.

Figure 10:
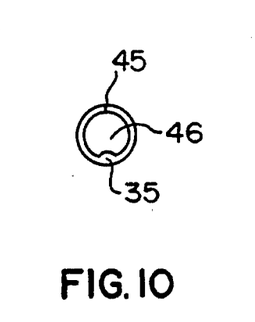
FIG. 10. This is a cross cut view of the endotracheal tube shown in previous fig of 7 in the area between the line 35–45. This shows a light bulb placed at 35.

FIG. 10. This is a cross cut view of the endotracheal tube shown in previous fig of 7 in the area between the line 35–45. This shows the cross cut of this tube in this spot which will be round and circular and it shows its lumen 46 with the bulb placed at 35.

Figure 11:
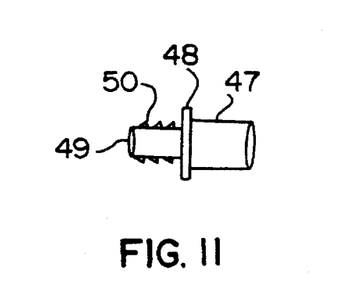
FIG. 11. This shows an adaptor that is to be inserted inside the tip of the endotracheal tube to allow it to be connected to the air bag or respirator.

FIG. 11. This shows an adaptor that is to be inserted inside the tip of the endotracheal tube to allow it to be connected to the air bag or respirator. This fig show the small end 49 which is to fit inside the opening 30 from FIGS. 7 & 8. It also shows how spikes of 50 may be made over this part in order to make the connection tight and stable. The wall 48 stands between the piece 49 and the 47. The end piece 47 will have an standard size to fit the tip of resuscitators and the air bags.

Figure 12:
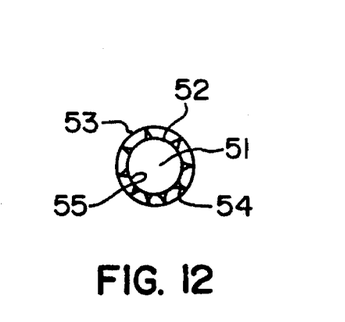
FIG. 12. This is a cross cut view of the endotracheal tube shown in previous fig of 8 in the area close to wall 40. This fig shows a soft wall outside of this tube with a small fortifications in it.

FIG. 12. This is a cross cut view of the endotracheal tube shown in previous fig of 8 in the area close to wall 40. This fig shows the inner lumen 51 which is inside the wall 55 and on the outer surface of the wall 52 of this endotracheal tube, there will be the short, soft wall 53 which has small fortifications of 54 to make it more stable. The over all shape of this wall 53 may be circular or even better to match the shape of the trachea in this area.

Figure 13:
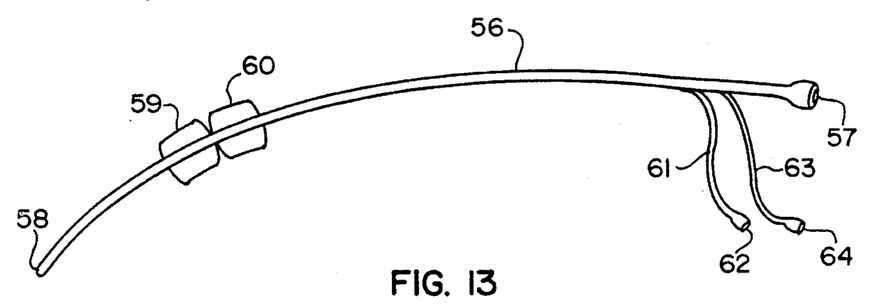
FIG. 13. This fig shows the side view of an esophageal tube which has a two balloons on its outer surface to prevent from stomach materials to come into pharyngeal area.

FIG. 13. This fig shows the side view of an esophageal tube which has two balloons in order to prevent from stomach materials to come into pharyngeal area under pressure or in case of significant gastroesophageal reflux. In this fig this unit is basically very similar to a commonly used high quality nasogastric tube, except it has two balloons of 59, 60 which are located on the outer surface of this tube (here refereed as esophageal tube) The balloon 59 can be inflated by inflation port of 62 and sealed and the balloon 60 can be inflated by inflation port of 64 and sealed. The consistency of these balloons will be soft to avoid damaging the esophagus. Here No. 58 shows the tip of the esophageal tube which will be placed inside the stomach. The body is shown by 56 and the outside opening by 57.

Figure 14:
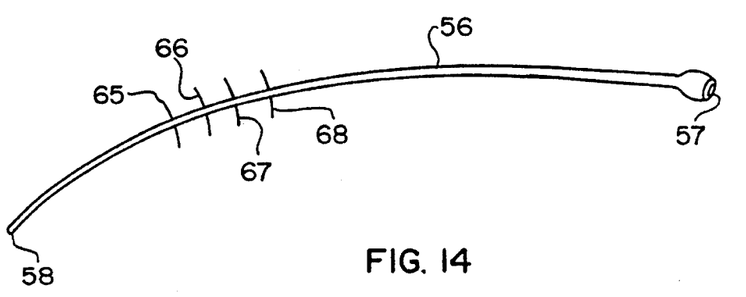
FIG. 14. This fig shows the side view of an esophageal tube similar to one shown in previous fig of 13 except this unit has a series of soft walls of 65, 66, 67, and 68. on it to prevent from food to come out from esophagus.

FIG. 14. This fig shows the side view of an esophageal tube which is very similar to one shown in previous fig of 13 except this unit has a series of soft walls of 65, 66, 67, and 68. Which are made from soft plastic and sized to occupy the space between the outer surface of this tube and the inner surface of the esophagus, in order to prevent from free flow of stomach materials to come into pharyngeal area under pressure or in case of significant gastroesophageal reflux. In this fig again the tip of this unit is shown by 58 and the main body of this unit is shown by 56 and the outside opening by 57.

Figure 15:
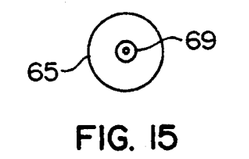
FIG. 15. This is a cross cut view of the esophageal tube shown in previous fig of 14, in the area close to the wall 65. This view shows the soil plastic wall around this tube.

FIG. 15. This is a cross cut view of the esophageal tube shown in previous fig of 14, in the area close to the wall 65. This view shows the cross cut of this tube in this spot with its outside surface shown by 69. and the wall 65 which will be a round and circular soft plastic wall (or any other working shape which may be different that the circular shape).

Figure 16:
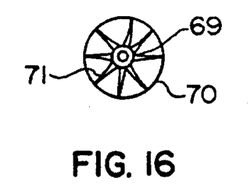
FIG. 16. This is a cross cut view of the esophageal tube similar to one shown in previous fig of 15 except this unit has a series of short fortified lines of 71 inside the wall.

FIG. 16. This is a cross cut view of the esophageal tube similar to one shown in previous fig of 15 except this unit has a series of short fortified lines of 71 which are to hold the wall 70 in more stable position and to prevent it to collapse due to pressure. In this fig the outer surface of this tube is shown by 69.

Figure 17:
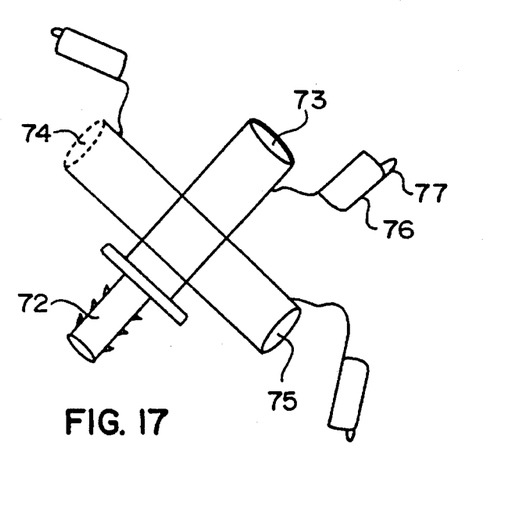
FIG. 17. This fig shows an adaptor with three opening that is to be inserted inside the tip of the endotracheal tube.

FIG. 17. This fig shows an adaptor that is to be inserted inside the tip of the endotracheal tube in order to allow it to be connected to the air bag or respirator. This unit is somewhat similar to the unit shown in FIG. 11. It has a small end 72 which is to fit inside the opening 30 from FIGS. 7 & 8. It also shows how specially directed spikes on the surface of this unit are located. These spikes are to secure stable connection between this piece and the endotracheal tube, they will allow easy insertion of piece 72 into piece 30 but would not allow it to be pulled out easily. This adaptor unit however has three connection openings which allows connection of air bag or the respirator to be done in either openings of 73, 74 and 75. Each one of these openings have a cap similar to one shown at 76 which can close the opening of that part tight. The cap 76 has a piece 77 to allow it to be pulled easily.

Figure 18:
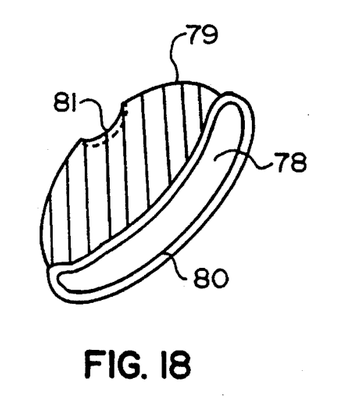
FIG. 18. Shows a plastic piece that is to be placed on the front of the neck between the upper border of the sternum and the cricuid cartilage and to cover this area and make the area under it dark for light from endo tracheal tube to be seen.

FIG. 18. Shows a plastic piece that is to stand on the front of the neck between the upper border of the sternum and the cricuid cartilage and to cover this area in order to prevent from the light to come into that area, so that the observer could look from window 81 easily to recognize the position of light from the trachea when the light of the endotracheal tube is tuned on. In this fig the body of this unit is shown by 79 and its side border which is nicely curved not to heart the neck by 80 and inner space by 78.

Figure 19:
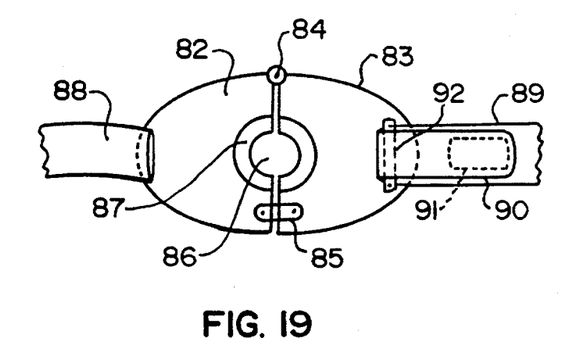
FIG. 19. Shows a piece which is to hold the endotracheal tube in place securely.

FIG. 19. Shows a piece made from plastic, latex, fabric or similar materials or their combinations. This piece is to stand in front of the mouth in order to hold the endotracheal tube (or an airway or a naso gastric tube) in place securely. This piece will allow the endotracheal tube to be placed in its open center 86 and be locked in this place. The inner wall of the piece 87 which surrunds this space may have small spikes to hold the endotracheal tube securely in place. This unit is made of two soft, flat shaped pieces of 82 & 83 that are hinged to each other at point 84. They will be locked by mean of lock 85 (which can be of any appropriate locking means). At the time of use the unit will be opened around the hinge 84 to have the endotracheal tube placed inside it and then locked securely by lock 85. Then this unit will be held in place securely by having the soft band/strap 88 to go from one side of it to go around the neck and to come and its end piece 90 go through the bridge 92 and make a U turn and be slicked on its own rear side by Velcro patch 91 or a similar fastening mean. The no 87 shows the piece that will hold the endotracheal tube in place.

Figure 20:
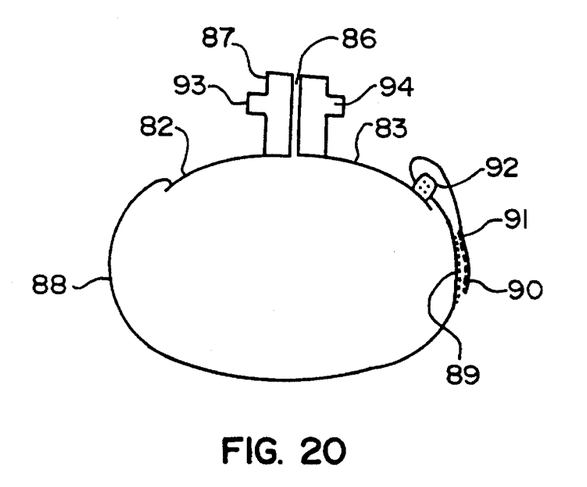
FIG. 20. This fig shows the side view of the piece shown in previous fig of 19.

FIG. 20. This fig shows the side view of the piece shown in previous fig of 19. in this view the side of pieces 82 & 83 is shown and it shows how the piece 87 is placed in the center and is above the surface, and has the opening 86 in its center. The expanded areas of 93 and 94 are to allow the sided 48 of the adaptor shown in FIG. 11 to be placed inside it for a maximum security. Please notice that in practice these adaptors are placed in the end of the endotracheal tubes (end 30 FIGS. 7 & 8). The band/strap 88 is shown and it extends and goes around the neck to become and be marked by 89. And its end piece 90 will go under the bridge 92 to make a U turn and be sticked on its own rear side by a Velcro patch 91 or a similar fastening mean.

Figure 21:
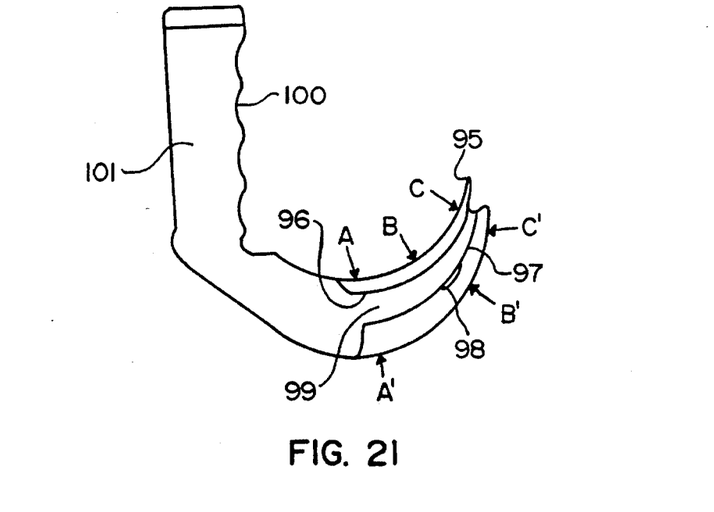
FIG. 21. This fig shows the side view of a new laryngoscope. Which has a curved walls to allow easy placement of the endotracheal tube in place.

FIG. 21. This fig shows the side view of a new laryngoscope. This unit is made from a handle 101 that is the place for battery. The handle has a front wall which may be shaped to allow a better grip with having the finger places 100. The unit has a curve A, B, and C to fit properly over the tongue and hold it in place. It has a tip 95 that will stay in front of the epiglottis and the surface next to it will be raised to match the rear surface of the epiglottis. It has a curved wall of 96 which is the right upper wall of this unit (it is shown in side cut views of 22 till 24 by 103). There is also another curved wall in lower right side 97 which is to direct the endotracheal tube to the tip of this unit in laryngeal area. This unit is to allow easy direction of the endotracheal tube toward the laryngeal area. In this fig the main wall of this unit is shown at 99. The upper wall by A, B and C. The confronting wall by A', B' and C' The side wall by 96 in the top and 97 in the lower side. The light by 98 which the tip of the light will aim toward the tip of this unit and laryngeal area. The light also will be placed out of the way and not to block the motion of the endotracheal tube in its way to the tip and not to tear the balloon of the endotracheal tube as well. In general the function of this new laryngoscope is to direct the endotracheal tube toward the vocal cord easily. It is also possible to park the end in this scope in half way in so that as soon as the unit is in place the endotracheal tube to be pushed to fit the opening of the vocal cord and placed properly.

Figure 22:
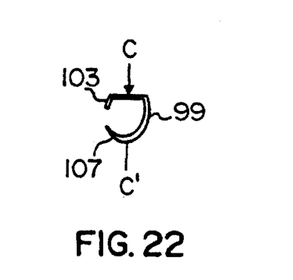
FIG. 22. This fig shows the cross cut view of the new laryngoscope which was shown in previous fig of 21. along the arrows C and C'.

FIG. 22. This fig shows the cross cut view of the new laryngoscope which was shown in previous fig of 21. This fig is a cut along the arrows C and C'this fig shows the base of this unit in C and its front wall by C' The main side by 99. The wall C turns to make the wall 103 which is to have a partial role in directing the endotracheal tube in proper direction. The wall C' has the extended curved wall of 107 which has an important role in directing the endotracheal tube in the right direction toward the laryngeal area.

Figure 23:
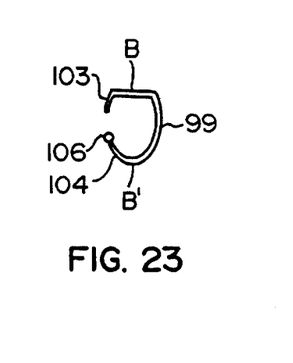
FIG. 23. This fig shows the cross cut view of the new laryngoscope which was shown in previous fig of 21. This fig is a cut along the arrows B and B'.

FIG. 23. This fig shows the cross cut view of the new laryngoscope which was shown in previous fig of 21. This fig is a cut along the arrows B and B'. this fig shows the base of this unit in B and its front wall by B' The main side by 99. The wall B turns to make the wall 103 which is to have a partial role in directing the endotracheal tube in proper direction. The wall B' has the extended curved wall of 104 which has an important role in directing the endotracheal tube in the right direction toward the laryngeal area. The 106 shows the place of the light.

Figure 24:
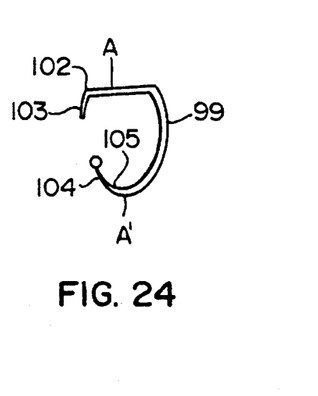
FIG. 24. This fig shows the cross cut view of the new laryngoscope which was shown in previous fig of 21. This fig is a cut along the arrows A and A'.

FIG. 24. This fig shows the cross cut view of the new laryngoscope which was shown in previous fig of 21. This fig is a cut along the arrows A and A'. this fig shows the base of this unit at A and its front wall by A' The main side by 99. The wall A turns to make the wall 103 which is to have a partial role in directing the endotracheal tube in proper direction. The wall A' has the extended curved wall of 104 which has an important role in directing the endotracheal tube in the right direction toward the laryngeal area. The no 105 shows the inner surface of the wall A' and its curve which will direct the tube in right direction specially when small amount of jelly is applied to the side of the endotracheal tube.

Figure 25:
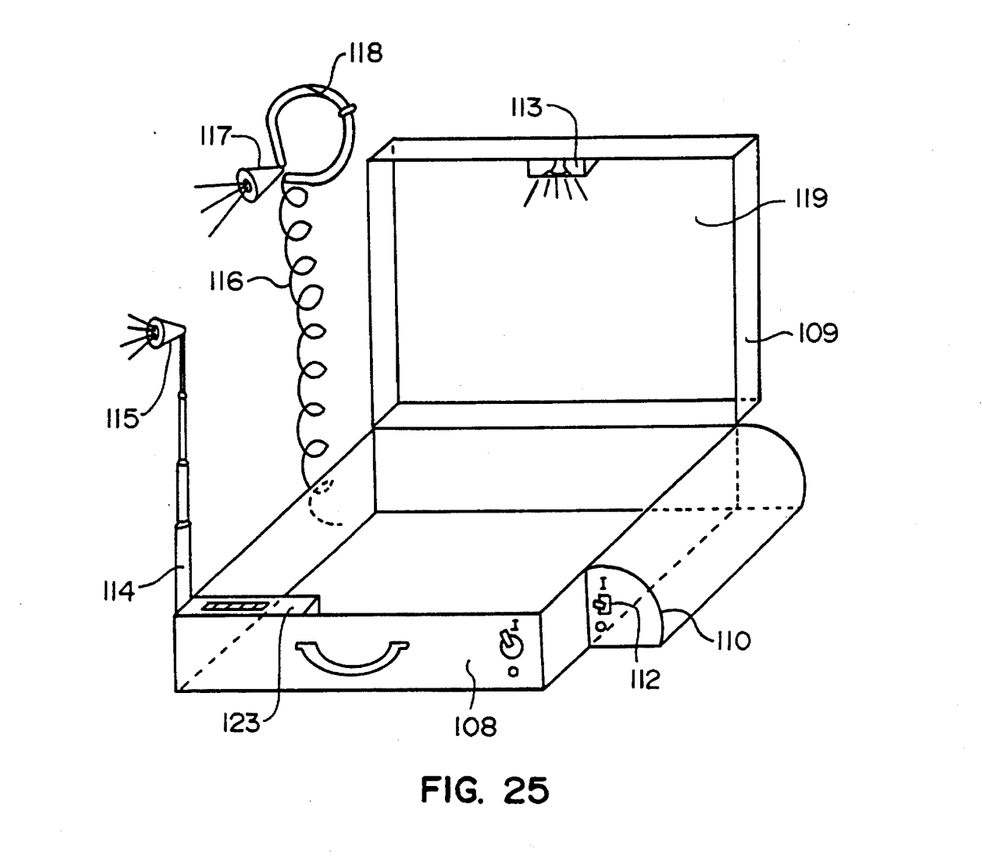
FIG. 25. This fig shows the general look of a special box which is to hold units mentioned in this text. This unit has lights and a suction 110 and proper space.

FIG. 25. This fig shows the general look of a special box which is to hold units mentioned in this text. This unit will have a basic lower part 108 and a top part 109 which both can held series of equipments. The lower part will hold at least one tray with properly placed units mentioned above on it, which will be sterile so that with removing its cover all of the clean materials for use can be available. The inner part of top piece may also give a home for a tray or hold certain numbers of the units inside cradles or by springs or elastic bands. In the inner side of it 119 it may have an informative chart as well which can be seen well by the light 113 conveniently placed inside a reflective mirror in the front of the upper lid. This light is to also give light to the surrounding area as well, so that at night as soon as the box is opened it will be source of a reasonable light in an environment that there is no light. Beside this light, since light is extremely important for such a work in darkness, two or more other sources of light will be also available for optional use, one 115 which will stand on the tip of an adjustable pole or telescopic antenna 114 which it can be make from many different means that will do this adjustable pole's job, such as folding units, springs etc. The other source 117 will be also available this light will have wire 116 connected to a male jack (not shown here) to be inserted inside a matching female jack that is connected to the source of electricity or battery. This light may have an adjustable band or strap that will hold this light on the front or in arm, around hand, around a tree, or any other reasonable pole. This light may also have a clamp to allow it to be clamped to a pole or part of dress as well. The 110 shows a compartment that is to hold a suction machine and its related collection bag (which the bag may be moved out). The switch 112 is to control its function.

Also the cassette player 123 is appropriately placed (in this case in left front corner) to help the person to have the main issues to be reminded to him.

Figure 26:
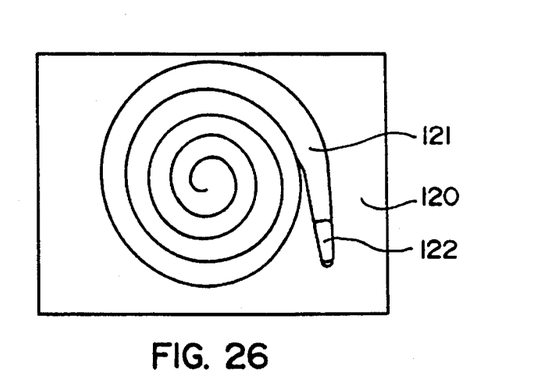
FIG. 26. This fig shows the bottom view of the same special box mentioned in previous fig of 25. This view shows a suction tube placed under this box.

FIG. 26. This fig shows the bottom view of the same special box mentioned in previous fig of 25. This view shows a tube which is connected to the suction machine will be properly placed so that it can be quickly pulled out to allow the suction to be utilized. It can be made that as soon as it is pulled the suction to start its function until will be turned off by its switch 112 from FIG. 25. This tube will be protected by a cover safely. In this view the base of the box is shown by 120, the tube by 121 and its tip which can be connected to other suction tips or be used alone by 122.

THE DETAILED EXPLANATION OF THIS INVENTION

This invention deals with making new units that is believed to be very beneficial during resuscitation of a patient, in order to allow more lives to be saved. A Cardiopulmonary resuscitation is a very extremely important event and the immediate life and death of a person is in stake. Commonly In less than an hour either that person will be saved to be treated to survive, or the body will turn to be cold, motionless, lifeless, to be taken to morgue and cremated. During this vital period many things happen at once and many problems happen all with together that they have to be dealt with properly to save a patient. Many procedures needs to be done almost simultaneously or one very rapidly after another in a very brief time to succeed. And the outcome of patient many times would depend to successful resuscitation and step by step success of these steps one after another. The time is truly important and every second of it has a significant value. One of the most important jobs in this circumstance is to have the airway of patient open, air flow and respiration to be maintained, and this is the part where my invention comes into play. The maintenance of the air way has many steps and one important one is to have the mouth opened and to prevent the tongue to block the air way of the patient. Commonly these patients needs to be intubated, and again the first step in this direction is to open the mouth of an unconscious and many times a hypoxic and seizing patient, which has his/her teeth clinched. Opening the mouth in this circumstance is not simple and a resistance has to be overcome and this is why many times patients loose parts or couple of their front teeth when the airway piece or the laryngoscope is used forcefully to overcome this resistance and provide the vitally needed air supply during the process of intubation. I have to mention that the presently used laryngoscopes are a rigid unit and when used as a lever, which many times happen in such circumstances and specially in hands of a none experienced staff who is working under extreme stress and urgency to maintain the airway, it will easily brake a piece or whole tooth or two.

Working in such circumstances and observing some of these problems has been an stimulant for the inventor to suggest the following solutions. There fore he proceeds here with his own models to solve some of these problems and these are as follows:

I. Mouth opening device.

This is a device to help to open the mouth of an unconscious or semi conscious person which cannot or does not allow his mouth to be opened for being helped. This (shown in FIG. 1) will be made from combinations of couple of pieces, first a combinations of an upper piece No. 2 FIG. 1 and a lower piece No. 1 fig one, which these pieces are in shape of a horse shoes or dentures and are to be placed outside of the teeth between outside of the teeth and the inner lip area in upper and lower palates. These pieces will be made from hard plastic or metal so that their basic skeleton will be hard and strong however their surface to have a layer of soft, rubbery, spongy or balloon cover to prevent it from injuring the gum. The lower piece may have a slightly raised rear tip at point 3 shown in FIG. 1. where it will be hinged to the other piece. So that the hinge will be higher than the lower piece's upper surface. Basically this combination piece will be placed in the mouth to help to push the upper and lower gums to be opened safely. For this opening function in the front or front lateral corners of these pieces, they will be connected to a lever or jacking system that will function to open the front of these two pieces easily. This jacking system may be mechanical or hydraulic, or by the following methods:

a. They may be opened or separated by hands.

b. They may be opened or separated by simple mechanical levers.

c. They may be opened or separated by a hydraulic or jacking system with use of fluid or air for separating these two pieces from each other and naturally the teeth as well.

This unit will help to open the mouth and to separate the teeth at least far enough to allow insertion of a vital piece called airway or its similar unit here introduced as a tongue presser inside the mouth to maintain the air way with preventing from the damaging the teeth. After this unit has opened the mouth, then the tongue presser will be used.

II. The tongue presser unit, and an airway.

The airway unit (shown in FIGS. 5 & 6) is made to press the tongue toward the base of the mouth and keep it out of way and specially from having the tongue to move back to close the airway. This unit will be made from a hard plastic with a curve and shape to match and fit over the tongue and be able to press it down and to keep that way. This piece will have a tube shape opening to allow the circulation of the air to occur immediately after insertion. This unit is to press the tongue toward the base of the mouth and keep it out of way and specially from having the tongue to move back to close the airway. This unit will have a piece 27 FIG. 5 which has indented outer surface to match and fit inside a unit similar to one shown in FIGS. 19 & 20 to hold it in place. Or it may have openings to allow straps to be connected to hold it in place.

A different model of this tongue presser may be made with having one or more specially designed balloons on its top surface FIGS. 2, 3 and 4 that are to function to open the mouth by pressing the mouth and tongue away from the center. These balloons will be in the sides to function like a jack, and its top surface to be a soft cover or a soft mattress kind. They will designed and be constructed to function as follows:

First: This balloon when inflated will press the tongue even further to have the mouth fully open and the tongue to stay out of the way. This will be done by inflation of the balloon part to work like a jack and raise not only itself (the balloon) but also to move and raise the parts that are attached to it (to this balloon) such as plate 16 FIGS. 2 & 3 so that then an open space No. 17 FIGS. 2 & 3 will be created in the middle of the mouth to allow the physician to work freely in this very vital condition that every second of it is important for saving patient's so many of his brain and heart cells. In some models a choice will be made to have the rear part of the tongue to be pressed before the front part of the mouth, so that this will prevent from the tongue to be pressed backward to close the throat and prevent from air exchange.

Second: this balloon will be made so that with increasing its size or volume the inner opening also to enlarge and allow more space inside this balloon and naturally inside the mouth of the patient to be used for having access to the pharynx area. This function will be done by having the side balloons to function such a raising poles, so that their height will get taller with their inflation. This open space then can be used for better insertion of the endotracheal tube and naso gastric tube and also for suctioning the pharynx area as well.

Third. In some models this combination may also have one, two or more special curved passages that The first passage; the naso gastric tube passage will be curved to direct a naso gastric tube and make it to go toward and slide from the rear surface of the pharynx and finally to be inserted into the esophagus. The second curve passage; The endotracheal tube passage will be curved to facilitate the endotracheal tube to move and be directed to the larynx area and finally into the trachea. The size of these passages may be chosen different so that it will not allow the user to use the tubes by mistake for example the size for the endotracheal tube will be larger than the esophageal part so that the endotracheal tube can not be inserted in that passage. Importantly color coding may be also used to show for example a partially blue colored endotracheal tube has to be inserted to the passage colored or marked by blue and the red colored esophageal tube has to be inserted in red marked or red colored passage. These are important since they will facilitate the procedure and prevent from an extremely vital time for that particular patient to be lost as well a mistakes to occur. Understanding function of the curves should not be difficult since we know how one point or a curve in an appropriate spot can change the course of move of a tube or a wire etc.

This unit may also have a tube or a third passage for being used to suction the secretions from the oro-pharyngeal area. Again the base of this unit may be made from a hard plastic plate and it has to stand on the top of the tongue. This piece may have an outer piece or a handle No. 22 FIG. 4 so that the motion of this handle will cause tilting of the whole unit to occur and to direct it the way which it is most useful. This function may be very useful in pressing the base of the tongue in order to open the area for a better visualization of the larynx.

The balloon mentioned above for opening the mouth may be made from one or a combinations of the balloons, and each one or a series of these balloons may have their own inflation port as well. This tongue presser may have a battery powered light in its tip or side for making the area to be lighted and visualized clearly.

Importantly in some models this unit may have an extension with a balloon to be pushed back and to be finally inserted into the esophagus in order to close its opening and to prevent from the stomach content to come out of esophagus and to contaminate the area. This particular extension may be made to slide on the surface of the rear wall of the pharynx by pushing its axle or handle and to have it moved and be placed in that area properly. A handle outside will allow this motion to be controlled to some degree. Also it may have a balloon or piece to close the opening of the nose in the oro-pharynx. This that will leave only the trachea open to be bagged for air exchange. The importance of this unit is that in a vital time it may eliminate the use of intubation that people may not be able to do it when they are not properly trained.

III. The new endotracheal tube.

Figure 27:
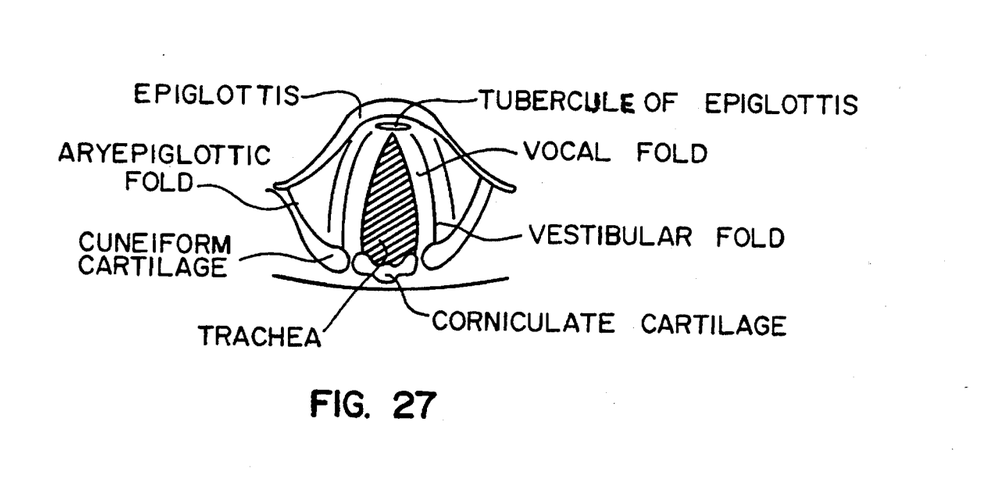
FIG. 27 is a view looking in the vicinity of the trachea.

This tube is a vital part of this unit. It will be a tube similar to a regularly and commonly used endotracheal tube, with its basic shape and construction, even with their balloons with their particular inflation port with a mini bulb connected to the inflation port similar to the commonly used endotracheal tubes which have a balloon in the tip for inflation. This mini bulb is to function as the indicator of the inner pressure. However there will be a significant improvements in its construction with having new pieces/parts or changes. These changes are introduced with intention to eliminate the problems that the inventor has seen to occur in patients who have been intubated. In inventors observation some of the patients who have been intubated had complained from a sore throat in that area for some time alter the intubation. The inventor have reached to a belief that there is a problem with construction of the presently used endotracheal tubes; and his reason is as follows: When we consider that the opening of the larynx (as shown by the dashed area in FIG. 27) is not circular and in fact has a shape which is very much like a triangle and even when it opens or is functional its shape changes to be similar to a larger triangle or perhaps a shape similar to a long triangle with a somewhat curved base. During intubation the endotracheal tube goes thorough the shaded area and stays between the vocal cords as long as it is in place. However the commonly used endotracheal tubes have a circular cross cut, so the inventor have reached to the conclusion that this big difference between the natural shape of the larynx from one side and the man made circular endotracheal tube from the other side causes a localized/focal uneven pressure in these vocal cords and the related area, making them to be stressed and then to suffer. Importantly having this fact in mind the new endotracheal tube is designed with a different idea in mind. These tubes then will have a special cross cut in the part (as shown in No. 43 FIG. 9) that matches and stands in the laryngeal area, so that it will match the anatomy of the larynx and its functional shape (he means the way which the vocal cords opens) in order to avoid pressing, stretching and stressing them unevenly in one spot or another, since he believes a divided pressure to the whole area or almost all area will prevent from a much higher pressure to one particular spot and so the outcome will be better. Importantly also in this new endotracheal tubes this laryngeal piece/area/part may be made from a strong material such as steel or a similar metal or materials in order to decrease the total thickness of the wall in this area so that the whole piece in this area to be the smallest sized possible (when the thickness of the wall is less naturally the size of the unit in this area will be smaller to cause less pressure, stress and discomfort). This metal wall may have a thin cover of plastic as well. Alternatively it may be only few pieces or a screen made of steel within a thin layer of plastic wall, which the steel is to fortify this part. Importantly the length of this piece may vary and in general it will be a long piece of about 3 to 5 cm or so in order to give a range which the tube may be moved without its shape to change in this area.

Furthermore this unit is to have another important adjuncts as well such as: having a small battery powered mini light (or a mini bulb). This mini bulb will be placed somewhere on the front wall of this endotracheal tube (as shown by No. 35 in FIGS. 7 & 8), in a position that when in proper place (the tip of the endotracheal tube about mid trachea area) this light to be in middle of the distance between the Cricoid cartilage and the upper notch of the sternum (the center bone of the chest). So that this light will play a very important role to allow the observer to notice the position of this tube by illumination of the light in the larynx area. (Importantly some other but similar means or techniques for verification of the position with use of electrical power and magnetic parts or power may also be utilized for this purpose as well).

This is believed to be very helpful in proper placement of this endotracheal tube and preventing it to be inserted shorter or longer than desired safe limit inside the trachea. This is an important issue to consider, since if the tip of the tube is too far in the trachea then the endotracheal tube can be in one big branch of the trachea (usually the right side one) or another, and if it is short in place it may come up easily to endanger the whole process, so both extremes are to be avoided. In practice and in the hospital the position of the endotracheal tube is commonly checked by having a X ray done by a portable X ray unit. However it is easy to consider that there is no X ray every where, besides it is hard and labor intensive and very bothersome as well (since patient has to be lifted to have X ray film to be placed under his/her chest with all the various tubes in place). It also takes time for the x ray to be done, developed and to be checked even in the best hospitals, with enough staff members. Furthermore if then the position of the tube needed to be changed the process of taking X ray starts all over again. This whole process is bothersome, labor intensive and expensive as well. For this reason the inventor believes that by having a mini light in the front wall of this endotracheal tube the user will be able to immediately notice and adjust the position of the endotracheal tube in place, since some gluing of the light can be visualized from the soft tissue of the neck located between the upper border of the sternum and the lower border of the cricoid cartilage. This area is an area with a soft tissue and rather thin cartilages, so that the inventor believes that it will allow such an illumination to occur (A hard cover similar to one shown in FIG. 18 with a hole 81 on its center, that fits the outer surface of the throat in this area may be used to keep the area dark and the person to look from the hole to see the light). This will allow the medical staff to be able to adjust the tube immediately if needed and most importantly also to be able to monitor its position easily and as many time as it is necessary since the motion of the patient may dislodge this unit many times. Importantly A small light may also be placed in the very end tip of such a endotracheal tube in order to allow the laryngeal area to be lightened and to allow insertion of the endotracheal tube to be done easily.

Importantly the light in the tip of this tube will also help in noticing that the tip of the endotracheal tube is not entering into esophagus as well which can be of significant help as well. Since if it is entering the esophagus the light will not come up as much.

The use of the light in the tip of this unit opens a new unknown possibilities as well. It bring this chance that the lights of different nature and magnitude may be used for different purposes as well. The lights have been used in medicine for killing germs such as ultra violet lights and for drying a wet surface such as heating lamps and the response of different germs to light may be different so it may give a chance in future to do some studies in this regard to experiment further, and may find a beneficial way of using them.

The third advantage or option in these endotracheal tubes will be an option which can be quite useful in these models, and it is to have a series of soft walls or webs (as shown in No. 40, 41 and 42 FIG. 8 and FIG. 12) instead of the inflatable balloon on the outside surface of these endotracheal tubes, that will function like a washers in the pistons of the engines of the cars. So that these will prevent from free motion of the air to occur or will make the volume of the leaking air around this unit so minimal that it will be negligible. This option or change may make these units cheaper, and simpler since it will eliminate the job of having to inflate the balloon (which takes time and need a syringe) and to have the inflation port in the way all the time.

It should also be said that the wires of this mini light will function to be as the x ray opaque material or marker as well, so that if there was a need for an x ray then they can be utilized for this purpose as well. They may be extended till the tip and may have a coil in that spot to show the tip better.

The models, nature, distance and make up of these webs or walls of this unit may be chosen to be different, they may be made to be a short, very soft walls, made from soft thin plastic that will play a role such as wall of a parachute, so that when the air is blown to or toward them it will make them to shape up and spread to resist the passage of the wind. This will be done more easily when these walls have a series of short but slightly thicker lines of supports in their construction (No. 54 FIG. 12). When a series of these walls or webs are placed on the outside surface of these tubes, they will collectively function as an effective barrier. Alternatively they may be made from combinations of two thin walls connected in their edges so that with pressure the space between them to expand and act as a balloon. Also they may be made to be like a series of soft, thin balloons as well to do the same job. Importantly the shape of these walls, webs or balloons will be dependent to the area of the trachea which these walls are expected to stay and their shape is to match and fit that part quite well. So their shape may not be completely circular and in some parts of it periphery may be somewhat flat, or may even have a different shapes to work best.

Importantly one of these webs or walls may be placed under the laryngeal area to prevent from air leak in that side. So it is believed by this inventor that the special shape of these endotracheal tubes in the laryngeal area as well as having such webs in position on the outer surface of these tubes, can eliminate the use of balloons in some of these models. Since when the endotracheal tube fits the space between the vocal cord and occupies them then there will be not much space for the air to leak, and the layer of plastic around the endotracheal tube may also be very helpful in this regard as well.

In another model of these endotracheal tubes instead of one tube may be chosen to have a combinations of the balloons or commonly to have two balloons. So that instead of having one long balloon, two smaller balloons side by side will be on the surfa ce of the endotracheal tube. Similar to two tires or rings standing one next to another. However each one of these balloons will have its own particular inflation line and its related mini bulb (similar to presently available endotracheal tubes, and this mini bulb is to allow checking the inner pressure). The two inflation ports can be connected by a unit similar to a threewaystopcock so that one can suction the air from one balloon to inflate the other balloon immediately. Or to inflate one balloon first and then to deflate the other one afterward. The advantage of having two balloons is that this will allow each balloon to be inflated intermittently so that there will be no persistent focal pressure by one particular balloon to one area of the trachea or another. This technique importantly will allow the surface of the trachea under the deflated tube to be relieved from stress, pressure and irritation during the period which the other tube is inflated, and this cycle will be repeated to diminish the total stress to the tracheal lining. The number of the balloons, their size thickness, their particular locations and the other important characteristics may be chosen to be different in different models as well.

Importantly the shape of this tube may vary during its length for example in lower end after laryngeal area it may have a round shape in front and somewhat flat shape in rear wall area the whole purpose it to match the shape of the inner trachea.

So that it would press less to a one particular spot and to be less traumatic to the mucosa of the area, and in cases when the plastic walls are used they easily match and fit the inner lumen. Also importantly the length of each different segment or piece or area such as laryngeal area or balloon area or the place of the light all may be adjusted to make different models and also models for different sex and size persons etc. It is believed that with these teachings and their modifications many models may be made which will be more useful than the present models.

The outer ends of these endotracheal tubes will accept an adaptor which will be similar to the commonly used adaptors but an improved version as well. These adaptors will have a series of teeth that will have a special shape similar to one shown in FIG. 11. These will allow the insertion to be easy but pulling them out to be difficult. This is to prevent from accidental dislogement of these adaptors and their connected tubes. A different adaptor may be made similar to one shown in FIG. 17. Which this adaptor will also have openings in its sides as well to facilitate the connection of the respirator tubings. Since in practice many times the connection of the endotracheal tube to the respirators are commonly done from the sides. An opening in the top No. 73 FIG. 17, will still exist for the bagging purposes and also suctioning as well. The side openings will have a cap that will close it securely to prevent from accidental opening.

It is important to notice that these improvements in the endotracheal tubes can be optional and different models of endotracheal tubes may be made to have one but not the other one of these options. For example the new unit may be made to have a circular cross cut or an oval shape cross cut in laryngeal area with a light and with balloon and not the web and another unit may be made to have special shape (low profile) in laryngeal area but with a light and the web instead of the balloon. etc. So there can be many different combinations and models that can be made to satisfy the need of a user.

It is also important to consider that the size of the trachea differs in different ages, sexes and even some races etc. Therefore it is essential to have these units to be made in different sizes and shapes to match each group. Therefore the size, shape, thickness, relative thickness of the area, the size and length and the distances of the different parts from each other, coloring of different parts, the material used and every other characteristics and important details of these units may vary.

Importantly in order to allow one or may be only few adaptors to be made and utilized with these tubes the end part of these units will be modified so that a universal adaptor or only a couple of them to be made and used in order to connect these tubes to the air bags or the respirators.

Color coding of the tip of these tubes and the adaptors will make it easy to chose the right size/br each one of them.

The means for holding the endotracheal tube or air ways in place.

Customarily and in observation of this inventor this job has not been easy and for this reason the inventor considers the following means and technique for holding these units in place.

No 1.

These new endotracheal tubes will be made to have a series of indentations on the outside surface of their outer end part (not shown in figures), close to the outer tip in order to allow a supportive piece to be connected to this area to hold this tube in place safely, securely and comfortably and to prevent from its displacement.

No 2.

There will be a matching part made from plastic, rubber, latex, fabric or similar materials or their combinations similar to the unit shown in FIGS. 19–20. So that this unit will have an inner tube shaped cradle 87 that will hold the base of endotracheal tube and its connected adaptor (similar to one shown in FIG. 11) in place inside itself securely. In order to prevent from dislodgment of the endotracheal tube. The inner surface of the cradle part of No. 87 this piece will have a series of spikes or indentations that will stick to the outer surface of the endotracheal tube to hold it in place securely. This unit will have a hinge in its rear side 84 FIG. 19 that will allow it to be opened in order to put the tubing in place then it will be closed so that its front end could be locked by different simple methods No. 85. And then a strap 88 will go from one end of this unit to go around the back of the neck and to come and go under a bridge 92 in the other end and to be slicked or fastened in its own side to have the whole unit stable in place around the neck.

No 3.

This unit shown in FIGS. 19–20 may also have a piece like a short tube shaped cradle C in order to hold the Nasogastric or Esophageal tube to be placed inside it in place. This cradle C will open to accept the endotracheal tube and then to be closed a small plastic piece will allow to adjust for the size of the endotracheal tube. This cradle C will be located in the nasal area which commonly the nasogastric tube is placed, it will be made to be rotated to right or left side to match the nasogastric tube in the right or the left side.

No 4.

This unit shown in FIGS. 19–20 may also be modified to stand in front of the nose and to have cradles A, that these cradles will accept and hold the endotracheal tube and an esophageal tube which are to be placed through the nose securely in place. However since in this case the endotracheal tube may be inserted in the right or the left nostril and the naso gastric tube in the other side, therefore two kinds of small cradles A will be made one for endotracheal tube placed in right nostril and nasogastric tube in the left side and the other one to have the reverse shape. Naturally in each case only one of these can be used. These cradles will have all of the components mentioned for piece 87 FIGS. 19–20 to hold these tubes in place securely although naturally the shape and direction of the cradle will be different when the tubes are inserted in the nose. This small cradle A will be placed inside a cradle B designed to accept it, and to be kept in place securely by a band or a door that will go over it.

IV. esophageal tubes.

The forth important part of this whole resuscitation unit is to have an esophageal tube that will have one or more balloons in its length around it. So that they can be appropriately placed around the tube to be inflated to stand and occupy the inner space of the esophagus. This esophageal tubes are to prevent from the contents of the stomach to be pushed out to the pharyngeal area and to contaminate all of the area which unfortunately commonly occur during a Cardiopulmonary resuscitation and is extremely disturbing and dangerous since the regurgitated food inside the mouth and throat area makes a messy place to work and aspiration of these materials into the lungs is nothing but asking for a big trouble so called Aspiration Pneumonia. Therefore it has to be avoided in all cost, and it is for prevention of such contaminations, that this particular esophageal tube is introduced so that it can be placed in the esophagus to prevent from regurgitation of the stomach contents as long as there is such a chance. This unit may be also used in any other conditions that there is a need to prevent from stomach contents to come up into the throat.

In another model of this esophageal tube the unit will be made from combinations of inflatable balloons. Which may be chosen to be two balloons, so that instead of having one long balloon two shorter balloons (Nos. 59 & 60 FIG. 13) standing side by side to be made on the outer surface of esophageal tube like having two tires or rings one next to another. Importantly each one of these balloons will have its own particular inflation port with a mini bulb connected to its thin inflation tube like the commonly used endotracheal tubes and it is to function as the indicator of the inner pressure. These two inflation tubes can be connected by a unit similar to a threewaystopcock so that one can suction air from one balloon to inflate the other balloon immediately. Or to inflate one balloon first and then to deflate the other one afterward. The advantage of having two balloons is that this will allow each balloon to be inflated intermittently so that there will be no persistent focal pressure by one particular balloon to one area. This technique importantly will allow the surface of the esophagus under the deflated tube to be relieved from stress during the period which the other tube is inflated, and this cycle will be repeated. The number of the balloons and their particular locations may be chosen to be different in different models as well. In general the size, shape, thickness, relative thickness of the balloons, the distances of the balloons from each other, the coloring of different parts, the material used and every other characteristics and important details of these units may vary. Interestingly a similar units may be made to be used in the colon during certain procedures to keep the area clean or to press the wall to prevent from bleeding after an spontaneous bleeding for from surface of tumor or after polypectomy. In the stomach it may be used to be cause a partial pressure for application of pressure in certain parts to prevent from bleeding as well. Or to cover a surface for healing. (One particular/interesting/untested use of these balloons may be for insertion inside the stomach from the nose or through a gastrectomy in order for the balloon to occupy the space of stomach to prevent from patient to eat much food and to make him/her to loose weight in morbid cases).

Importantly like the endotracheal tube this esophageal tube may also be made with having a series of appropriately placed circular walls or webs similar to one shown in FIG. 14 to function such as walls, or similar to the fabric of parachute so that when the secretions of the stomach are pushed against them this force to make them to shape up and spread and to resist the passage of the food materials. This function may be done more effectively when these walls are made to have a series of short but slightly thicker lines (No. 71 FIG. 16) of supports in their construction. When a series of these webs (Nos. 65, 66, 67 and 68 FIG. 14) are placed on the outside surface of these tubes they will collectively function as an effective barrier, to prevent from regurgitation of the stomach contents to occur. These walls may be also be made with combinations of two walls connected to each other along their outer edges so that when pressed to act like a thin balloon as well. They may also be made to be like a series of soft thin balloons to perform the intended function.

Like the endotracheal tubes these esophageal tubes may also be made to have a series of indentations on the outside of their surface in order to allow a support piece to be connected to it and to hold this tube in place safely, securely and comfortably and prevent from its displacement. This support piece will be made to be hold this tube and to be strapped securely around the neck.

The new laryngoscope: This is a unit designed to allow easier insertion of the endotracheal tube in place, the intention here is to have a funnel type walls that will automatically direct the endotracheal tube to the opening of the larynx or its vicinity so that with gentle manipulation it could be entered inside the trachea. The unit will have a light bulb properly placed to lighten the area and not to stand on the way of the endotracheal tube and not to cause perforation of is balloon as well. This unit is to be made with a special shape shown in FIG. 21 with a flat surface that has a curve A, B and C to go over the tongue and press it to keep the tongue out of the way so that the tip of the laryngoscope would reach the front of the epiglottis. This unit may also have a raised wall on the inner surface of the C area in order to match the level of the rear surface of the epiglottis. So that when in place the surface of this laryngoscope in this area and the rear surface of the epiglottis to be in the same plane, in order to facilitate the insertion of the endotracheal tube in this area so that the tip of the laryngoscope not to hit the tip of the epiglottis. This unit is to have a light in the side no 98 to lighten the area. However importantly this unit is to have the curved wall shown by 96 and 97 in this fig of 21 and shown in the cross cut fig of 22, 23 and 24. In FIG. 22 it is shown by 103–107 in FIG. 23 by 103–104 in FIG. 24 by 103 and 104. The purpose of this wall is to function as a funnel as mentioned earlier, so that all together it will be a mean to direct the endotracheal tube to the larynx due to its special curve, for an easy placement. This laryngoscope may have a small piece or soft band in area A–C in order to hold the endotracheal tube in the position which will be ready to be pushed forward for placement inside the larynx. So that there will be no need for inserting the endotracheal tube thorough the mouth after the vocal cord is seen. This band may expand or simply tear during the advancement of the laryngoscope. In some models the side walls 103–104 from FIG. 24 and their extensions may be made to be from soft plastic for this purpose. This technique can be of great help and time saver as well. This unit may be made from a strong clear plastic (may have pieces of metal for fortification purpose) so that its wall will allow visualization of the area to occur and its wall not to block the views. The light may be properly placed in its side or the tongue side so that not to stay in way of the tube and not to damage the balloon of the endotracheal tube also not to block the vision as much as possible. The handle of this unit will be made to give a good and comfortable grip. This unit may be made to be disposable and instead of battery it may have a wire to be connected to a battery pack. The combination of a place for battery in the handle and a connection wire to receive the electricity from a battery pack may also be present. Some models of this unit may not have a light but to rely on the light of the endotracheal tube itself, or the airway.

The remote control laryngoscope: This is a unit that is to be utilized for insertion of endotracheal tubes. This unit will have a series of fiberoptic fibers or similar materials that from an ocular part it will allow the tip of the unit to be visualized. This unit may or may not have light of its own. This unit will have control knobs or handles to allow the motion and the direction of the tip of the unit to be controlled and changed. At the time of insertion of the endotracheal tube the endotracheal tube will be pulled over this new laryngoscope so that the tip of the unit could be directed to be inserted inside the trachea. And the observation of the tip as well as rotation of the tip in a favorable direction will allow this to happen. As soon as the tip was in place then endotracheal tube which was already placed over this tube will be sled over the shaft of this scope to be directed and gently placed properly inside the trachea. As soon as the endotracheal tube is in place the laryngoscope will be pulled out. The other alternative will be to use a controlable guide wire (with having wires inside guidewire that gives special directions to it) that can be manipulated in order to be easily inserted inside the trachea and then to slide and feed the endotracheal tube to finally be placed in the right place. The use of new laryngoscope and such guide wires are more beneficial in cases that the neck of the patient should not be manipulated very much for one reason or another such as neck injuries or so. A softer endotracheal tube may also be made to be used with these new laryngoscope or guide wires to avoid the need for moving patients neck.

A Special box. this will be a box similar to one shown in FIG. 25. This box will be made with a series of special ancillary units to make it a very helpful unit for this and similar jobs. First it will have a battery operated lights in the front of its lids that will turn on, when the lid is opened to stand straight up (a switch may be also available for turning them off). The bulb of this unit will be appropriately placed inside a proper reflecting mirror in order to provide light to the scene of operation as well. This unit may also have a wire and a proper jack to allow it to be plugged to a car cigarette lighter or car battery. Also a connection to an electricity sources as well to provide a source of electricity if was needed. Also importantly a small projector lights such as one shown by 115 and 117 in that fig of 25, will be also added to this unit to be connected to the battery of this unit by way of a wire 116 that its end will have a male jack to be plugged into a female jack in the side of this box and this light will allow the chance of using it in dark for more lighting. This projector will have an elastic band or a strap to allow it to be placed around the head of the user and to be nicely positioned to stand as a head lamp in proper position to allow him to see inside the mouth or the scene he is working. Or around the hand or around a pole or any other similar places. It may also have a clamp to allow it to be hooked to parts of the dress, cloth, poles or other parts as well. Even may have a magnet to allow it to be sticked on the side of car or similar places. The other lamp will have an adjustable pole made from a controlable or adjustable pole/stand such as telescopic antenna or spring or similar means. To allow it to be raised, rotated, tilted so that could be properly positioned to function as an effective light source if needed.

The suction unit. This box or some models of it will have a battery operated suction unit with related tubes as well, which will be used to suction the secretions and regurgitant materials from the mouth of the patient and to deliver it into a soft plastic bag. The tubing of it may be appropriately placed in the outer surface of this box or its side or base under a protector lid in order to allow it to be taken out quickly and to be functional in a very short time. The collection bag of this suction unit may be placed in the side or similar places as well. This suction may be planed to be turned on as soon as the lid is opened a switch may be used to turn it off. The function of this unit is vital since many times there is a need for suctioning the materials and even saliva from the oropharynx area, otherwise the chance of aspiration and aspiration pneumonia will be high.

A small oxygen tank. This will be quite helpful to provide the oxygen in the very early stages of the resuscitation which more likely patient has been hypoxic. Related tubings will be already connected ready to be used.

The cassette player. importantly this box will also have a cassette player number 123 FIG. 25, which will be conveniently placed in this box so that it will start to broadcast a tape with a step by step directions and important issues about how the pieces to be used and the air way to be maintained in a sick patient and in a very practical matter. So that all of important points that a person needs to know to be mentioned and this be to be of great practical help in a difficult circumstance at night in middle of no where, which a better help and more educated people are not just simply around.

These units will have a series of different size endotracheal tubes in its pack to allow a proper size to be chosen. And they can be of great help and an asset in certain circumstances such as picnic places, special tours, factories, restaurants etc. Naturally some familiarity with function of these units are needed and which should be done in each large groups which may be target of sudden death. These units can be part of these educations as well, they may be used in schools for such extremely important issues, and the teaching of CPR to follow. In a more complete models medications may also be added and to have another tray that will have those meds and tapes to continue explanations and directions as well. A series of tapes may be chosen for different problems such as treatment of drowning, snake bites, burns, cuts, nasal bleeding, chocking etc.

Very importantly a patient monitor, a defibrilator and an ECG machine, an external pacemakers, a fax machine, a modem a portable telephone, a phone system that shows the picture of the person during the talk, a series of medications, ordinary surgical equipments and similar things all may be added to these units to make them a truly efficient and a life saving units. means may be added as well.

It is important to consider that the airway securing system as introduced is to do one single very important job; that is to provide and maintain airway and air/oxygen to a sick person who will otherwise die. These may save life a person specially if we consider that the problem with AIDs virus has made the people extremely unwilling to do mouth to mouth resuscitation and therefore presence and availability of such units will be extremely vital in most of such circumstances. These primary units are to be packed in a convenient disposable trays which will be sterile so that with removal of one single cover of this tray all these units will be exposed for use, so that there will be no need for wasting the time to open each one separately. The pieces and their places will have numbers, color codings, informative writings, figures, charts and similar things to show the easiest way and the common way of using these pieces and their purpose. The charts may be placed in the inner surface of the lid that the light of the box will make it to be seen well. The numbers can be made as such:

1. the mouth opener.
2. the airway or tongue pressure.
3. the suction unit if needed.
4. the laryngoscope.
5. the endo tracheal tube.
6. the air bag.
7. the esophageal tube.
8. the unit which hold them in place securely. etc.

These boxes will also have an air bag included (which allows the bagging of the patient to be done) and an easy and clear illustrated directions are also to be available in a very convenient and useful way to be used in circumstances which the better equipments with experienced persons to use them are not available.

It should be noted that the stress of the inventor here is all to cut the time which a patient will be anoxic, since during this period a constant progressive and many times irreversible damage will occur to the cells of brain, heart and kidney and in fact many other organs as well. So to shorten this period is extremely important and it may cut the general cost of saving a patient many folds. Prevention of brain loss, heart damage, kidney failure, aspiration pneumonia each is saving thousands of dollars. Also in this system the gloves, four by fours, goggles, face masks and some basic medications and similar things will be also provided as well. These units will have a series of different size endotracheal tubes in its pack to allow a proper size to be chosen. And they can be of great help and an asset in certain circumstances such as picnic places, special tours, factories, restaurants etc.

These combinations may also prove to be an extremely useful equipments in circumstances such as man made or natural disasters. Such as wars, earthquakes etc. One day these units may save a son, a daughter, a husband or wife of a human being.

It will be of great pleasure for the inventor to hear that these models one day caused saving life of a single person. It will be of much greater joy if they caused saving many lives and for that he prays.

I claim:

1. An endotracheal tube comprising a walled tube having an external wall surface and comprising intubation passage means extending lengthwise from a proximal external end of the endotracheal tube to a distal internal end of the endotracheal tube for intubation of a patient, means disposed on said external wall surface of said walled tube proximal to a location on said walled tube where said passage means comprises an opening adapted to provide communication of said passage means with a trachea of a patient, but distal to a laryngeal area of a patient, for obstructing a trachea of a patient while leaving said intubation passage means open, said walled tube comprising a region that is adapted to be disposed in a laryngeal area of a patient and that has a transverse cross sectional shape that closely conforms to the transverse cross sectional shape of a laryngeal area of a patient for minimizing stress applied to a laryngeal area of a patient because of placement of the endotracheal tube, and including a source of illumination disposed on said walled tube that is adapted to be disposed between a cricuid cartilage and a notch of a sternum of a patient when said distal internal end of said walled tube is placed substantially in a mid-tracheal area of a patient to illuminate through a patient's neck so that proper placement of the endotracheal tube can be ascertained by visual observation by personnel treating a patient.

2. An endotracheal tube as set forth in claim 1 in which said region of said walled tube that is adapted to be disposed in a patient's laryngeal area has a transverse cross sectional shape that comprises a pair of converging sides that converge at a rounded apex, and a further side that joins said converging sides opposite said apex.

3. An endotracheal tube as set forth in claim 2 in which further side has a convex exterior.

4. An endotracheal tube as set forth in claim 1 in which said means disposed on the external wall surface of said walled tube proximal to a location on said walled tube where said passage means comprises an opening adapted to provided communication of said passage means with a trachea of a patient, but distal to a laryngeal area of a patient, for obstructing a trachea comprises an inflatable balloon means.

5. An endotracheal tube as set forth in claim 4 in which said balloon means comprises two separate balloons each of which is separately inflatable from the other by its own respective inflation port that is externally located.

6. An endotracheal tube as set forth in claim 1 in which said means disposed on the external wall surface of said walled tube proximal to a location on said walled tube where said passage means comprises an opening adapted to provide communication of said passage means with a trachea of a patient, but distal to a laryngeal area of a patient, for obstructing a trachea comprises at least one annular wall disposed transverse to said walled tube, said annular wall being constructed and arranged to allow its perimeter to substantially conform to an inner wall surface of a trachea.

7. An endotracheal tube as set forth in claim 6 in which said means disposed on the external wall surface of said walled tube proximal to a location on said walled tube where said passage means comprises an opening adapted to provide communication of said passage means with a trachea of a patient, but distal to a laryngeal area of a patient, for obstructing a trachea comprises a succession of such annular walls spaced apart along the length of said walled tube.

8. An endotracheal tube as set forth in claim 6 including reinforcements extending between said walled tube and said annular wall, said reinforcements being distributed circumferentially spaced apart around said walled tube.

9. An endotracheal tube as set forth in claim 1 including a shroud for external placement on a patient's neck to facilitate visual observation of said source of illumination by shielding ambient external light from an area of a patient's neck over which the shroud is placed.

10. An endotracheal tube as set forth in claim 1 including a further source of illumination at the distal end of the endotracheal tube to provide for improved illumination during the intubation process of placing the endotracheal tube in a patient, thereby to eliminate the need for using a lighted laryngoscope.

11. An endotracheal tube comprising a walled tube having an external wall surface and comprising intubation passage means extending lengthwise from a proximal external end of the endotracheal tube to a distal internal end of the endotracheal tube for intubation of a patient, means disposed on said external wall surface of said walled tube proximal to a location on said walled tube where said passage means comprises an opening adapted to provide communication of said passage means with a trachea, but distal to a laryngeal area of a patient, for obstructing a trachea while leaving said intubation passage means open, including a source of illumination disposed on said walled tube that is adapted to be disposed between a cricuid cartilage and a notch of a sternum of a patient when said distal internal end of said walled tube is placed substantially in a mid-tracheal area of a patient to illuminate through a patient's neck so that proper placement of the endotracheal tube can be ascertained by visual observation by personnel treating a patient.

12. An endotracheal tube as set forth in claim 11 including a shroud for external placement on a patient's neck to facilitate visual observation of said source of illumination by shielding ambient external light from an area of a patient's neck over which the shroud is placed.

13. An endotracheal tube as set forth in claim 12 including a further source of illumination at the distal end of the endotracheal tube to provide for improved illumination during the intubation process of placing the endotracheal tube in a patient, thereby to eliminate the need for using a lighted laryngoscope.

14. An endotracheal tube comprising a walled tube having an external wall surface and comprising intubation passage means extending lengthwise from a proximal external end of the endotracheal tube to a distal internal end of the endotracheal tube for intubation of a patient, means disposed on said external wall surface of said walled tube proximal to a location on said walled tube where said passage means comprises an opening adapted to provided communication of said passage means with a trachea, but distal to a laryngeal area of a patient, for obstructing a trachea while leaving said passage means open, and a fitting engaged with said walled tube at said proximal external end of the endotracheal tube wherein said fitting comprises a tube end port engaged with said walled tube and multiple ports communicated with said tube end port to provide for multiple connections of external equipment to said passage means, and in which said tube end port has external barbs engaging said walled tube to resist separation, and there are three of said multiple ports communicated with said tube end port, including one or more caps for selectively closing one or more of said multiple ports.

* * * * *